United States Patent [19]
Lopez-Avila et al.

[11] Patent Number: 6,111,108
[45] Date of Patent: Aug. 29, 2000

[54] EXTRACTION OF BIOLOGICALLY ACTIVE COMPONENTS FROM CAMPTOTHECA ACUMINATA WITH SUPERCRITICAL FLUIDS

[75] Inventors: Viorica Lopez-Avila, Cupertino; Janet V. Benedicto, San Jose, both of Calif.

[73] Assignee: Midwest Research Institute, Kansas City, Mo.

[21] Appl. No.: 09/107,713

[22] Filed: Jun. 30, 1998

Related U.S. Application Data

[60] Provisional application No. 60/051,405, Jul. 1, 1997.
[51] Int. Cl.[7] .................................................. C07D 491/22
[52] U.S. Cl. ................................................................ 546/48
[58] Field of Search .................................................. 546/48

[56] References Cited

U.S. PATENT DOCUMENTS

| | | | |
|---|---|---|---|
| 4,400,398 | 8/1983 | Coenen et al. | 426/429 |
| 4,744,926 | 5/1988 | Rice | 260/412.2 |
| 5,169,868 | 12/1992 | Rice | 554/193 |
| 5,210,240 | 5/1993 | Peter et al. | 554/11 |
| 5,252,729 | 10/1993 | De Crosta et al. | 540/18 |
| 5,547,673 | 8/1996 | Bombardelli | 424/195.1 |
| 5,750,709 | 5/1998 | Castor | 546/348 |

*Primary Examiner*—Mukund J. Shah
*Assistant Examiner*—Brenda Coleman
*Attorney, Agent, or Firm*—Chase & Yakimo, L.C.

[57] ABSTRACT

An extraction technique for the isolation of Camptothecin from plant matter of the Camptotheca Acuminata. The plant matter is loaded into a high-pressure vessel of a supercritical fluid extraction system and is pressurized with supercritical carbon dioxide to extract plant waxes or other waste. A modifier, preferably methanol, is then added resulting in the extraction of the Camptothecin into the solvent.

11 Claims, 2 Drawing Sheets

EXTRACTION OF BIOLOGICALLY ACTIVE COMPONENTS FROM CAMPTOTHECA ACUMINATA WITH SUPERCRITICAL FLUIDS

This application claims benefit of U.S. Provisional Application No. 60/051,405, filed Jul. 1, 1997.

BACKGROUND OF THE INVENTION

The potential of the Camptotheca Acuminata, a tree native to China, as a source of cancer drugs was first noted by M. Wall and J. Hartwell in 1958. In 1966, M. Wall isolated Camptothecin from the bark of Camptotheca Acuminata. In the 1970's, a Camptothecin analog (i.e., sodium salt) was tested by the National Cancer Institute (NCI) in humans and was found to have serious toxic side effects; consequently, NCI decided to halt all clinical trials. Nonetheless, research to find other less toxic Camptothecin derivatives continued, and second-generation derivatives including 9-amino-Camptothecin, Topotecan, and Camptothecin 11 or CPT-11 are currently being evaluated in clinical trials. Smith Kline Beecham Pharmaceuticals discovered Topotecan, and Pharmacia Upjon is marketing CPT-11. Research Triangle Institute synthesized and evaluated 9-nitro-Camptothecin in 1986, and the Stehlin Foundation researched it, potential of use in humans.

Camptothecin constitutes approximately 0.4 percent of the dry weight of young leaves of the Camptotheca Acuminata tree. This level is 1.5-fold higher than that of the seeds and 2.5-fold higher than that of the bark as reported by McKnight and coworkers, *Planta Medica* 1994, 60, 558–560. It has also been reported by Buitelaar and coworkers, *Plant Cell Tissue and Organ Culture* 1992, 28, 11–18, that Camptothecin was produced in cell suspension cultures from Camptotheca Acuminata stem parts (no Camptothecin was detected in the media of the cell suspension cultures).

The extraction method published by Monroe and Wall (see FIG. 1) is complex, time-consuming, costly, uses large quantities of solvents and not efficient enough as far as yield is concerned.

SUMMARY OF THE INVENTION

This invention describes an improved extraction technique for isolating Camptothecin from plant material (e.g., leaves, bark, root, seeds) of the Camptotheca Acuminata tree, and cell suspension cultures of Camptotheca Acuminata.

According to this invention, a novel method has been developed for the extraction of Camptothecin from plant material. This objective is achieved in a two-step process by replacing the hot heptan,e specified in the process outlined in FIG. 1 with supercritical carbon dioxide at 200–400 atm and 40–60° C., and by replacing the ethanol extraction/chloroform partitioning step by using supercritical carbon dioxide at about 400 atm modified, in the preferred embodiment, with 5–30 percent methanol. This results in a simpler, environmentally friendly process which produces high yields.

DETAILED DESCRIPTION

This invention provides an improved extraction technique for isolating Camptothecin from plant material (e.g., leaves, bark, root, seeds) of the Camptotheca Acuminata tree, and cell suspension cultures thereof.

Figure 1:
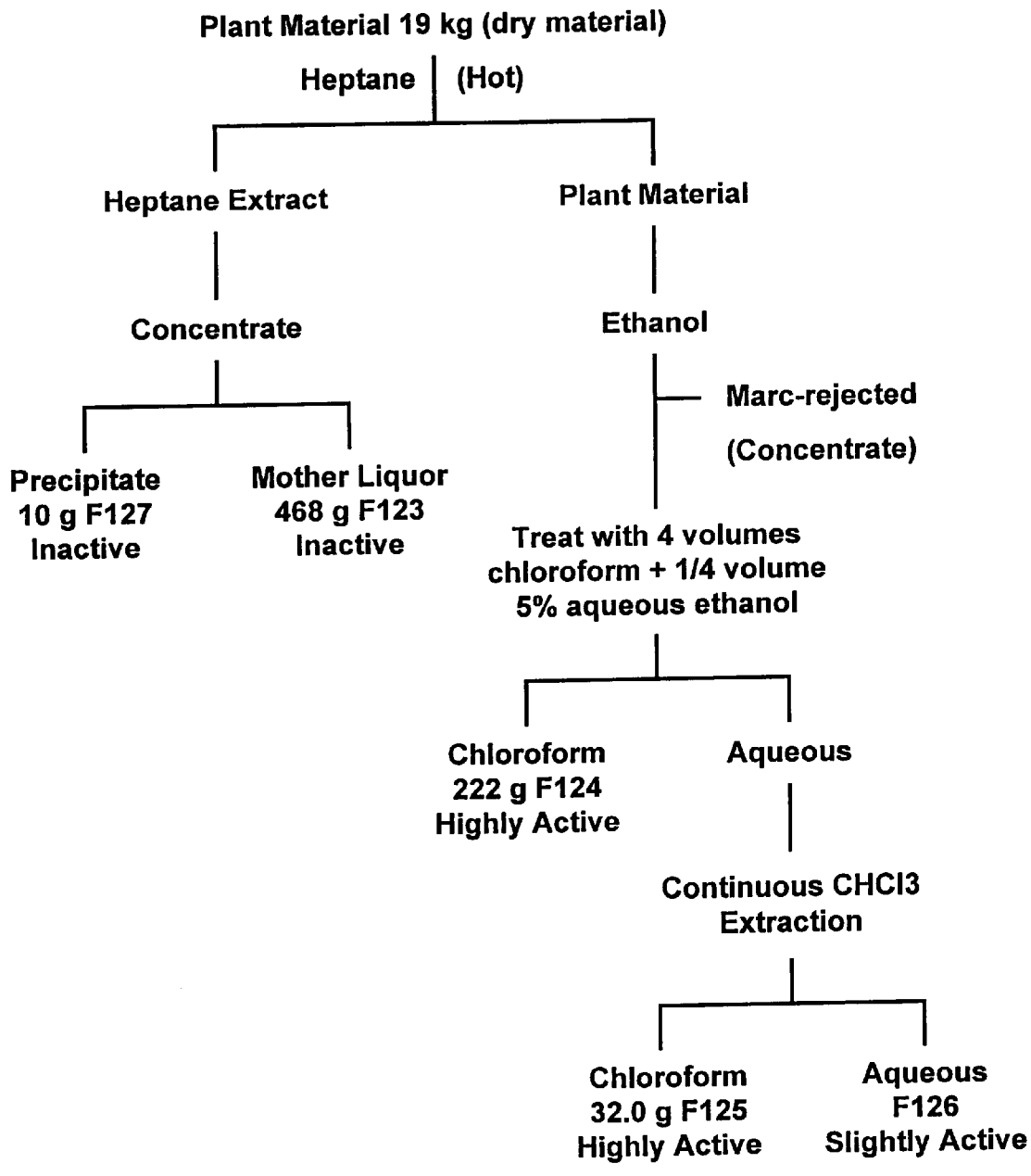
FIG. 1 is a flow chart of a prior art extraction method published by Monroe and Wall.
Figure 2:
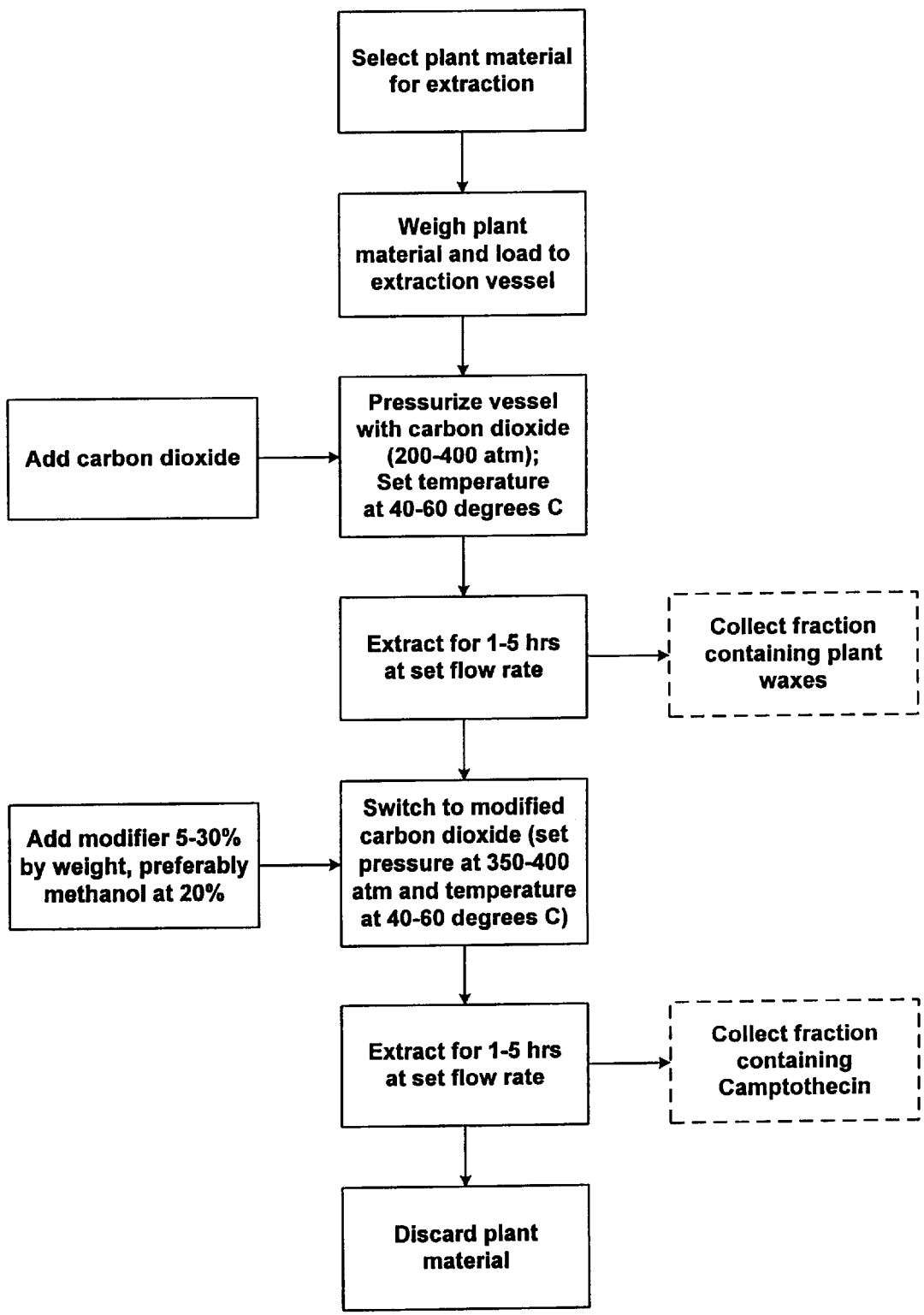
FIG. 2 is a flow chart showing an embodiment of the extraction method of the present invention.

As illustrated in FIG. 2, plant material (fresh or dried, milled or pelletized if desired) is loaded into a high-pressure vessel of a supercritical fluid extraction system ("SFE") and is pressurized with supercritical carbon dioxide at 200–400 atm (preferably 400 atm) at 50 to 60° C. A minimum ratio by weight of carbon dioxide to the feed material on the order of 100:1 is preferred. As soon as the pressure reaches the preselected value, the outlet valve of the extractor is opened and the flow rate is set so as to maintain the pressure at the preselected value. The initial extracted material containing the plant waxes is collected first.

With the system pressurized, modifier is added to carbon dioxide at 5 to 30 percent (by weight) and the extraction is continued at 350 to 450 atm (preferably 400 atm) and 40 to 60° C. as shown in FIG. 2. The preferred modifier is methanol but other modifiers (e.g., alcohols, ketones, chlorinated solvent, water) may be used.

The extraction continues until no more Camptothecin is extracted from the plant material. The system is then depressurized, exhausting the carbon dioxide, and the plant material is discarded. The extraction product, comprising the modifier/solvent and dissolved Camptothecin, which has been collected in a separator may be analyzed for Camptothecin yield. The modifier may be removed by evaporation.

Benefits of this process include the following:

(1) Supercritical carbon dioxide can replace the organic solvents currently used (heptane and chloroform).

(2) Carbon dioxide is nontoxic, nonflammable, environmentally friendly, and relatively inexpensive.

(3) Preliminary experiments performed with freeze-dried leaves and fresh leaves indicate that SFE yields range from 50 to 85 percent.

(4) The process can be automated.

We claim:

1. A method for isolating Camptothecin, said method comprising the steps of:

(a) selecting a substrate for extracting Camptothecin therefrom, (b) loading the selected substrate into an extraction vessel, (c) introducing carbon dioxide into said vessel in contact with said substrate and at a temperature and pressure exceeding its critical temperature and pressure to cause the carbon dioxide to reach a supercritical state, whereby to produce an initial extraction product, (d) separating said initial extraction product from a remaining portion of said substrate, (e) adding a solvent to said vessel and pressurizing the vessel to at least approximately 350 atm to extract Camptothecin from said portion of the substrate and provide a subsequent extraction product containing the extracted Camptothecin, and thereafter (f) collecting said subsequent extraction product from the vessel.

2. The method as claimed in claim 1, wherein said substrate includes the Camptotheca Acuminata.

3. The method as claimed in claim 1, wherein said substrate includes cell suspension cultures of the Camptotheca Acuminata.

4. The method as claimed in claim 1, wherein the temperature and pressure of said carbon dioxide in step (c) are at least about 200 atm and 40° C. respectively.

5. The method as claimed in claim 1, wherein said step (d) effects separation for at least one hour.

6. The method as claimed in claim 1, wherein said solvent is selected from the group consisting of an alcohol, ketone, chlorinated hydrocarbon or water.

7. The method as claimed in claim 1, wherein said solvent includes methanol.

8. The method as claimed in claim 6, wherein said solvent is 5–30% by weight of said carbon dioxide.

9. The method as claimed in claim 1, wherein said step (e) effects extraction for at least one hour.

10. A method for isolating Camptothecin, said method comprising the steps of:

(a) selecting a substrate for extracting Camptothecin therefrom, (b) loading the selected substrate into an extraction vessel, (c) introducing carbon dioxide into said vessel in contact with said substrate and at a temperature of at least approximately 40° C. and a pressure of at least about 200 atm to cause the carbon dioxide to reach a supercritical state, whereby to produce an initial extraction product, (d) separating said initial extraction product from a remaining portion of said substrate, (e) adding a solvent to said vessel and increasing the pressure thereof to approximately 350–450 atm to extract Camptothecin from said portion of the substrate and provide a subsequent extraction product containing the extracted Camptothecin, and thereafter (f) collecting said subsequent extraction product from the vessel.

11. The method as claimed in claim 10, wherein said step (e) effects extraction for at least one hour.

* * * * *